(12) United States Patent
Xiao et al.

(10) Patent No.: US 12,122,744 B1
(45) Date of Patent: Oct. 22, 2024

(54) METHOD FOR SEPARATING FLAVOKAWAIN AND KAVALACTONE, KAVALACTONE, AND MICROENCAPSULATED KAVALACTONE

(71) Applicant: Shaanxi Jiahe Phytochem Co., Ltd., Shaanxi (CN)

(72) Inventors: Hong Xiao, Shaanxi (CN); Xiaoying Wang, Shaanxi (CN); Yu Zhang, Shaanxi (CN); Chunde Wang, Shaanxi (CN); Beilei Dang, Shaanxi (CN); Yu Ji, Shaanxi (CN); Yuanyuan Wei, Shaanxi (CN)

(73) Assignee: Shaanxi Jiahe Phytochem Co., Ltd., Shaanxi (CN)

( * ) Notice: Subject to any disclaimer, the term of this patent is extended or adjusted under 35 U.S.C. 154(b) by 0 days.

(21) Appl. No.: 18/598,033

(22) Filed: Mar. 7, 2024

(30) Foreign Application Priority Data

Jul. 11, 2023 (CN) .......................... 202310845986.1

(51) Int. Cl.
*C07C 45/81* (2006.01)
*A61K 36/67* (2006.01)
*C07D 309/32* (2006.01)

(52) U.S. Cl.
CPC .............. *C07C 45/81* (2013.01); *A61K 36/67* (2013.01); *C07D 309/32* (2013.01); *C07C 2601/16* (2017.05)

(58) Field of Classification Search
CPC .... C07C 45/81; C07C 2601/16; C07D 309/32
See application file for complete search history.

(56) References Cited

U.S. PATENT DOCUMENTS

2003/0099756 A1* 5/2003 Gow ...................... A61K 36/67
426/615
2023/0248795 A1* 8/2023 Ross ................... A61K 31/4375

FOREIGN PATENT DOCUMENTS

CN 102846721 A 1/2013
CN 115501143 A 12/2022

OTHER PUBLICATIONS

Ranjith W. Dharmaratne, H., et al. "Kavalactones from Piper Methysticum, and Their 13C NMR Spectroscopic Analyses." Phytochemistry, vol. 59, No. 4, Feb. 2002, pp. 429-433. ScienceDirect, https://doi.org/10.1016/S0031-9422(01)00443-5. (Year: 2002).*

(Continued)

*Primary Examiner* — Valerie Rodriguez-Garcia
*Assistant Examiner* — Kyle Nottingham
(74) *Attorney, Agent, or Firm* — Cooper Legal Group, LLC

(57) ABSTRACT

The present application relates to a technical field of separating kavalactone and flavokawain, and in particular, to a method for separating flavokawain and kavalactone, kavalactone, and microencapsulated kavalactone. The separation method includes: S1. grinding root of *piper methysticum*, extracting by supercritical carbon dioxide and collecting a residue for later use, in which an extraction temperature is 45-50° C. and an extraction pressure is 4-8 MPa; S2. extracting the residue by supercritical carbon dioxide, and collecting extracted oil for later use, in which an extraction temperature is 60-80° C. and an extraction pressure is 20-50 MPa; S3. performing re-extraction and adsorption on the extracted oil to obtain a primary product of the kavalactone; and S4. crystallizing the primary product of kavalactone to obtain the kavalactone. The obtained kavalactone is used for microencapsulated kavalactone.

6 Claims, 1 Drawing Sheet

(56) References Cited

OTHER PUBLICATIONS

Abu, Nadiah, et al. "The Flavokawains: Uprising Medicinal Chalcones." Cancer Cell International, vol. 13, No. 1, Dec. 2013, p. 102. DOI.org (Crossref), https://doi.org/10.1186/1475-2867-13-102. (Year: 2013).*

Ashraf-Khorassani, M., et al. "Supercritical Fluid Extraction of Kava Lactones from Kava Root and Their Separation via Supercritical Fluid Chromatography." Chromatographia, vol. 50, No. 5-6, Sep. 1999, pp. 287-292. DOI.org (Crossref), https://doi.org/10.1007/BF02490830. (Year: 1999).*

Lopez-Aila, Viorica, and Janet Benedicto. "Supercritical Fluid Extraction of Kava Lactones from Piper Methysticum (Kava) Herb." Journal of High Resolution Chromatography, vol. 20, No. 10, Oct. 1997, pp. 555-559. DOI.org (Crossref), https://doi.org/10.1002/jhrc.1240201007. (Year: 1997).*

\* cited by examiner

METHOD FOR SEPARATING FLAVOKAWAIN AND KAVALACTONE, KAVALACTONE, AND MICROENCAPSULATED KAVALACTONE

CROSS-REFERENCE TO RELATED APPLICATION

This application is a priority and benefit of China patent application serial no. 202310845986.1, filed on Jul. 11, 2023. The entirety of China patent application serial no. 202310845986.1 is hereby incorporated by reference herein and made a part of this specification.

TECHNICAL FIELD

The present application relates to a technical field of separating kavalactone and flavokawain, and in particular, to a method for separating flavokawain and kavalactone, kavalactone, and microencapsulated kavalactone.

BACKGROUND ART

Piper methysticum is a plant originated in the South Pacific, belonging to Solanaceae (Piperaceae Giseke). Kava drink is traditionally a suspension of kava root extract, which is a drink for religion or celebration in history. However since kava drink has a characteristics of relaxing, it is increasingly becoming an usual drink among South Pacific islanders.

It was reported in literatures that, kavalactone in the kava extract has some functions such as stress alleviation, sleeping improvement, anxiety management, memory reinforcement, inflammation inhibiting, immune system adjustment and cancer prevention. As far back as 1990, *piper methysticum* for a treatment of anxiety disorders was approved by the German Federal Health Agency. In addition, *piper methysticum* was added to the Plant Pharmacopoeia in England, and to new edition of the United States Pharmacopoeia in America, and *piper methysticum* is listed as over-the-counter or prescription drugs.

At the same time, the use of kava has also a certain degree of death traps: in the late 1990s, there were rare and severe cases of liver toxicity among kava users, which also draw public attention to safety (Stevinson C, Huntley A, Ernst E. *A systematic review of the safety of kava extract in the treatment of anxiety. Drug Saf.* 2002; 25 (4):251-61.). The viewpoint can further be supported by a recent study result (Narayanapillai S C, Leitzman P, O'Sullivan M G, Xing C. *Flavokawains a and B in kava, not dihydromethysticin, potentiate acetaminophen induced hepatotoxicity in C57BL/6 mice. Chemical research in toxicology.* 2014; 27 (10):1871-6.). The study indicates that two types of chalcone based chemicals such as flavokawains A and flavokawains B in the Kava can improve liver toxicity induced by paracetamol.

In some existing methods for preparing the kavalactone, for example, by using supercritical carbon dioxide, specific steps are as follows: grinding root of *piper methysticum*, adding to an extraction kettle, setting 30-50° C. of temperature and 15-25 MPa of pressure, feeding liquid $CO_2$ and an entrainer, performing supercritical extraction to obtain an extract, analyzing the extract under conditions on 50-60° C. of temperature and 5-10 MPa of pressure, dissolving the obtained extract in ethyl acetate, passing through a short alumina column to obtain a liquid, recovering the ethyl acetate from the liquid, and drying at low temperature to obtain the product. For another example, the kavalactone is prepared by using solvent extraction. The specific steps are as follows: grinding root of *piper methysticum*, adding 5-10 times ethanol solution with a concentration of 60-90%, performing ultrasonic extraction for 2-3 times to obtain extracted liquid, performing vacuum concentration on the obtained extract, adding the concentration solution to macroporous resin for adsorption, first performing eluting to remove impurities by using 40-60% of ethanol solution having 3-5 times volume of the column, then performing eluting by using 90% of ethanol solution having 3-5 times volume of the column, further collecting the obtained elution solution, performing vacuum concentration, drying the concentration solution with alumina, loading the dried concentration solution into the column, performing gradient elution with ethanol solution, collecting efficient ingredients, and drying by vacuum concentration to obtain the kavalactone.

However, the above methods focus on a preparation of kavalactone, without mentioning the separating of kavalactone from flavokawain, such that a higher total amount of flavokawains A and flavokawains B is present in the obtained flavokawain, imposing potential hazards to human health. Therefore, it is a necessary to provide a method for separating kavalactone, flavokawain A and flavokawain B, thereby ensuring a sufficient separation of kavalactone, flavokawain A and flavokawain B.

SUMMARY

In order to improve a separation efficiency of kavalactone, flavokawain A and flavokawain B, the present application discloses a method for separating flavokawain and kavalactone, kavalactone and microencapsulated kavalactone.

In a first aspect, the present application provides a method for preparing flavokawain and kavalactone, adopting the following technical solution:
a method for separating flavokawain and kavalactone, including the following steps:
S1. grinding root of *piper methysticum*, extracting by supercritical carbon dioxide and collecting a residue for later use, in which extraction temperature is 45-50° C. and an extraction pressure is 4-8 MPa;
S2. extracting the residue by supercritical carbon dioxide, and collecting the extracted oil for later use, in which extraction temperature is 60-80° C. and extraction pressure is 20-50 MPa;
S3. performing re-extraction and adsorption on the extracted oil to obtain a primary product of the kavalactone; and
S4. crystallizing the primary product of kavalactone to obtain the kavalactone.

By adopting the above technical solution, the ground primary product of the roots of *piper methysticum* is processed by supercritical carbon dioxide on conditions of low temperature and low pressure in the step S1 of the present application. Since polarity of flavokawain A and flavokawain B is low and polarity of kavalactone is high, the flavokawain A and the flavokawain B of low polarity are mainly extracted and the kavalactone of high polarity is remained in the residue by the technology, so as to achieve the separation of kavalactone and flavokawain (flavokawain A and flavokawain B), which can achieve the separation of flavokawains (flavokawain A and the flavokawain B) accounting for 40-60 wt % of total amount and kavalactone; in which, there are a large amount of kavalactone in the residue, and a large amount of flavokawain A and flavokawain B in the extracted solution of S1. Based on the S1, S2 is further performed. The residue is processed by supercritical carbon dioxide on conditions of high temperature and high pressure in the step S2, such that the flavokawain A and the flavokawain B of low polarity are remained in the residue and the kavalactone of high polarity is mainly extracted by the technology, further achieving the separation of kavalactone and flavokawain (flavokawain A and flavokawain B). By the step S2, the content of kavalactone in the extracted oil is 75-85 wt %, while containing flavokawains (flavokawain A and flavokawain B) of 2-5 wt %. The extracted oil is further processed, in which, a large amount of flavokawain (flavokawain A and flavokawain B) and kavalactone are firstly separated by re-extraction process, then flavokawain (flavokawain A and flavokawain B) and kavalactone are further separated by adsorption process, and crystallizing to obtain the kavalactone. The content of flavokawain (flavokawain A and flavokawain B) is 0.05-0.18 wt %.

In addition, kavalactone of the present application is a mixture of six compounds, including: 1. Methysticin; 2. Dihydromethystcin; 3. Kavain; 4. Dihydrokavain; 5. Yangonin; and 6. Desmethoxyangonin. Flavokawain refers to a mixture of two components, and the two components are respectively flavokawain A and flavokawain B.

Optionally, in the S1, extraction time is 60-180 min, flow rate of supercritical carbon dioxide is 10-50 mL/min; and in the S2, extraction time is 120-180 min, flow rate of supercritical carbon dioxide is 60-100 mL/min.

By adopting the above technical solution, in the S1, raw materials are processed by the conditions of low temperature and low pressure in combination with the above extraction time and flow rate of supercritical carbon dioxide, which is one of basic conditions of fully separation the flavokawain (flavokawain A and flavokawain B) of low polarity and the kavalactone of high polarity. In the technology parameters, if the extraction time is too short (less than 60 min) and flow rate of supercritical carbon dioxide is too slow (less than 10 mL/min), it will result in excessive residual flavokawain in the residue, which will affect the separation efficiency of flavokawain and kavalactone; if the extraction time is too long (more than 180 min) and flow rate of supercritical carbon dioxide is too fast (more than 50 mL/min), it will cause that the excessive kavalactone processed by S1 is extracted together with the flavokawain, leading to less kavalactone remained in the residue, which will affect a yield of kavalactone. Therefore, it is necessary to achieve the separation of kavalactone and flavokawain in the residue by the extraction time of 60-180 min, flow rate of supercritical carbon dioxide of 10-50 mL/min in combination with a process condition of low temperature and low pressure. In the S2, the residual is processed by a condition of high temperature and pressure in combination with the above extraction time and flow rate of supercritical carbon dioxide, achieving a full separation of flavokawain and kavalactone, so that the flavokawain can be remained in the residue and the kavalactone enters into extracted oil. In the technology parameters, if the extraction time is too short (less than 120 min) and flow rate of supercritical carbon dioxide is too slow (less than 60 mL/min), it will result in excessive residual kavalactone in the residue, which will affect the separation efficiency of flavokawain and kavalactone and yield of kavalactone; if the extraction time is too long (more than 180 min) and flow rate of supercritical carbon dioxide is too fast (more than 100 mL/min), it will cause that kavalactone is dissolved in the extractant, while other components (substances with high polarity except for kavalactone and flavokawain) are further extracted together, thereby affecting the yield and purity of the obtained kavalactone. Therefore, in the S2, it is necessary to achieve the separation of kavalactone and flavokawain in the residue by the extraction time of 120-180 min, the flow rate of supercritical carbon dioxide of 60-100 mL/min in combination with a process condition of high temperature and high pressure, so that the content of the flavokawain is merely 0.05-0.09 wt % in the crystal of the kavalactone.

Optionally, the re-extraction process of S3 includes the following steps: dissolving the extracted oil in a first solvent, performing re-extraction by using a re-extraction solvent to obtain an extraction mother solution, in which the first solvent is 80-95 Vol. % of ethanol solution or 80-95 Vol. % of methanol solution, and the re-extraction solvent is one or more of N-hexane, petroleum ether, and ether.

By adopting the above technical solution, difference of polarity between kavalactone and flavokawain (flavokawain A and flavokawain B) can result in differences of solubility in different solvents, such that kavalactone is further separated with flavokawain (flavokawain A and flavokawain B), and more kavalactone is remained in the extraction mother solution. The above first solvent and re-extraction solvent are selected to achieve a better separation efficiency. In the technical solution, the first solvent can be 80-95 Vol. % of ethanol solution, such as: 80 Vol. % of ethanol solution, 82 Vol. % of ethanol solution, 85 Vol. % of ethanol solution, 88 Vol. % of ethanol solution, 90 Vol. % of ethanol solution, 93 Vol. % of ethanol solution or 95 Vol. % of ethanol solution; or the first solvent can be 80-95 Vol. % of methanol solution, such as: 80 Vol. % of methanol solution, 82 Vol. % of methanol solution, 85 Vol. % of methanol solution, 88 Vol. % of methanol solution, 90 Vol. % of methanol solution, 93 Vol. % of methanol solution or 95 Vol. % of methanol solution.

Optionally, an adsorption temperature in step S3 is 50-90° C.

By adopting the above technical solution, activity of adsorbent can further be improved by heating, thereby improving the effect of adsorption; and the adsorption can be achieved more efficiently and sufficiently by the heating process. In the above technical solution, adsorption temperature can be 50-90° C. in the adsorption process of S3, such as can be 50° C., 54° C., 58° C., 61° C., 65° C., 69° C., 73° C., 76° C., 80° C., 82° C., 85° C., 88° C. or 90° C.

Optionally, an adsorbent used in the adsorption in step S3 is one or more selected from a group consisting of silicone, alumina, activated carbon, C18, polyamide, and Sephadex LH-20.

By adopting the above technical solution, flavokawain (flavokawain A and flavokawain B) and kavalactone can further be adsorbed to the adsorbent, such that kavalactone can be further separated with flavokawain (flavokawain A and flavokawain B), improving the effect of separation.

Optionally, the adsorbent is a mixture of C18, silicone and activated carbon in a weight ratio of (0.8-1.5):(4.5-5.8):(3-4).

By adopting the above technical solution, separation efficiency of kavalactone and flavokawain (flavokawain A and flavokawain B) can be further improved by the above preferred adsorbent. In the above technical solution, a weight ratio of C18, silicone and activated carbon can be 0.8:(4.5-5.8):(3-4), 1.0:(4.5-5.8):(3-4), 1.2:(4.5-5.8):(3-4), 1.5:(4.5-5.8):(3-4), (0.8-1.5):4.5:(3-4), (0.8-1.5):4.7:(3-4), (0.8-1.5):5.1:(3-4), (0.8-1.5):5.3:(3-4), (0.8-1.5):5.6:(3-4), (0.8-1.5):5.8:(3-4), (0.8-1.5):(4.5-5.8):3, (0.8-1.5):(4.5-5.8):3.5 or (0.8-1.5):(4.5-5.8):4.

Optionally, addition amount of the adsorbent is 1-5 wt % of the obtained extracted oil of S2, and extraction time is 4-8 h.

Optionally, crystallizing in step S4 includes the following steps: dissolving the primary product of the kavalactone in a second solvent, heating, then adding a third solvent, stirring until there is a crystal appearing, standing for solid-fluid separation to obtain a kavalactone crystal.

By adopting the above technical solution, polarity of solvent is changed, such that kavalactone can be gradually appeared, however flavokawain (flavokawain A and flavokawain B) is remained in the residue, further achieving the separation of kavalactone and flavokawain (flavokawain A and flavokawain B), so that flavokawain (flavokawain A and flavokawain B) has a less residual in the kavalactone crystal.

Optionally, heating temperature in step S4 is 40-80° C.; the second solvent can be one or more selected from a group consisting of methyl acetate, methyl butanone, methanol, ethanol, acetone, and ethyl acetate; and the third solvent is one or more selected from a group consisting of petroleum ether, n-hexane, and dichloromethane.

Optionally, volume ratio of the second solvent and the third solvent is (8.5-10):1.8.

Optionally, standing time in step S4 is 12-24 h.

In a second aspect, the present application provides a kavalactone, adopting the following technical solution:

A kavalactone, the kavalactone is obtained by using the above separating method; and the total amount of flavokawain A and flavokawain B in the kavalactone is 0.05-0.18 wt %. Further, a total amount of flavokawain A and flavokawain B in the kavalactone is 0.05-0.09 wt %.

By adopting the above technical solution, kavalactone of the present application is a product obtained by a full separation with flavokawain A and flavokawain B, among them, the content of flavokawain (flavokawain A and flavokawain B) is rare, only 0.05-0.18 wt %, and the content is merely 0.05-0.09 wt % in a further preferred technical solution, therefore safety of the kavalactone is high.

In a third aspect, the present application provides a microencapsulated kavalactone, adopting the following technical solution:

a microencapsulated kavalactone, including an inner core and an outer cladding layer, in which the raw material of the inner core includes the above kavalactone.

By adopting the above technical solution, oil component remaining in the kavalactone can be adsorbed by addition of accessories, such that the kavalactone is placed in a more dried environment, the microencapsulated kavalactone can further avoid direct contact with air, so as to prevent the kavalactone from spoiling during storage, thereby improving shelf life thereof, and ensuring storage and transportation more convenient. In addition, after microencapsulated treatment, the kavalactone is in a water dispersed state, which is more beneficial to digestion and absorption of the human body, and may improve its utilization.

Optionally, raw material of the outer cladding layer includes an excipient which is a combination composed of emulsified starch and dextrine in a weight ratio of (1-10):1.

Optionally, a method for preparing the microencapsulated kavalactone includes the following steps:

I. Preparation of oil phase: dissolving the kavalactone in 85-95 Vol. % of ethanol solution, then concentrating into a grease, and storing at 75-82° C. for later use.

Preparation of water phase: dissolving the excipient into hot water for later use;

The weight ratio of the excipient and the kavalactone is (10-200):10.

II. Mixing the water phase and the oil phase under an action of high-speed shearing, and then spray drying to obtain the microencapsulated kavalactone.

In the microencapsulated kavalactone prepared of the present application, content of the kavalactone can be adjusted by adding appropriate amount of excipients according to different requirements. For example, content of the kavalactone in the microencapsulated kavalactone is more, a small amount of excipients can be added; for example, content of the kavalactone in the microencapsulated kavalactone is less, a large amount of excipients can be added.

Further optionally, a temperature of the hot water for dissolving the excipient is 80-100° C.

Further optionally, time of the high-speed shear in II is 30-60 min, rotary speed of which is 8000-12000 rpm; the temperature during the spray drying is 80-90° C.

Optionally, raw material of the microencapsulated kavalactone further includes a film former, a weight ratio of the film former and the excipient is (1-3):1000.

Further optionally, the film former can be one or more of acacia senegal, xanthan gum, and carrageenan. Further optionally, the film former can be acacia senegal.

Further optionally, when raw material of the microencapsulated kavalactone further includes the film former, the method for preparing the microencapsulated kavalactone includes the following steps:

I. preparation of oil phase: dissolving the kavalactone in 85-95 Vol. % of ethanol solution, then concentrating into a grease, and storing at 75-82° C. for later use;

preparation of water phase: dissolving the excipient into hot water for later use; The weight ratio of the excipient and the kavalactone is (10-200):10.

II. Mixing the water phase, the oil phase and the film former under an action of high-speed shear, and then spray drying to obtain the microencapsulated kavalactone.

In summary, the present application can achieve at least the following beneficial effects:

1. Supercritical extraction of two steps is used in the present application, in the supercritical extraction of the first step, most flavokawain (flavokawain A and flavokawain B) are separated from the kavalactone, during the treatment, the kavalactone is remained in the residue and the flavokawain is in the extracted oil; then supercritical extraction of the second step is used, such that most of the kavalactone and the flavokawain are further separated in the residue. In the treatment, the kavalactone is in the extracted oil, while parts of the flavokawain are further in the extracted oil. By the subsequent treatment of re-extraction and absorption, a further separation of the kavalactone and the flavokawain in the extracted oil can be further separated, and content of the flavokawain in the obtained kavalactone crystal is 0.05-0.18 wt %. In some technical solutions, content of the flavokawain in the obtained kavalactone crystal is 0.05-0.09 wt %, lower than 0.1 wt %.

2. The extractant and the adsorbent used in the treatments of re-extraction and absorption are also preferred in the present application, further improving separation efficiency of the kavalactone and the flavokawain.

3. The obtained kavalactone crystal is further treated by microencapsulation to improve storage time of the kavalactone, and is beneficial to transportation. While the microencapsulated kavalactone is in the water dispersed state, which is more beneficial to digestion and absorption of the human body, and improving its utilization.

DETAILED DESCRIPTION

Figure 1:
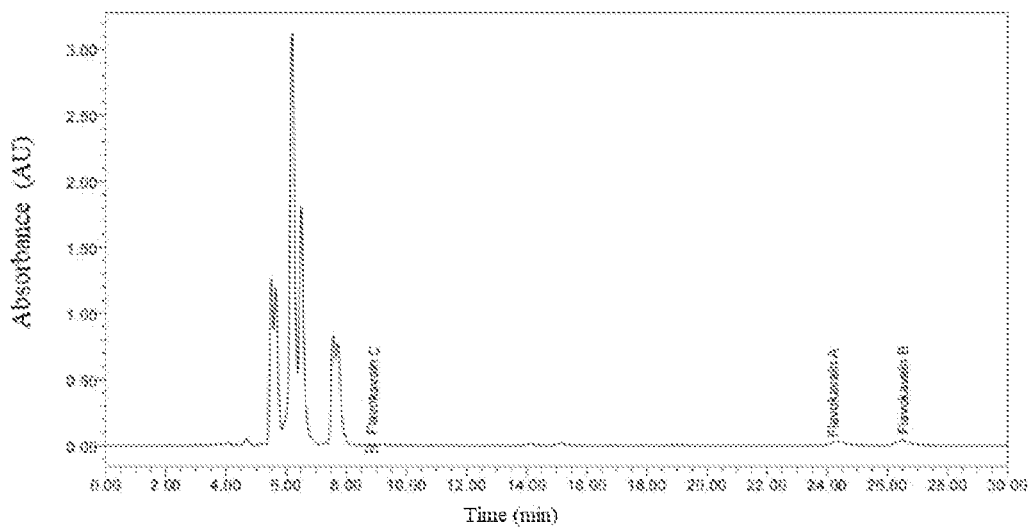
FIG. 1 is a liquid chromatogram of flavokawain in a kavalactone crystal obtained by separation method of Example 2.
Figure 2:
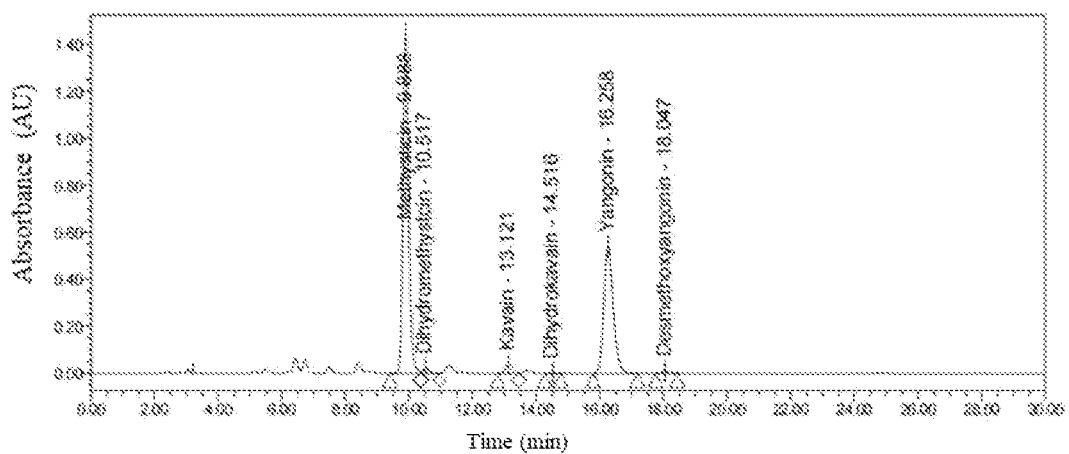
FIG. 2 is a liquid chromatogram of kavalactone in a kavalactone crystal obtained by separation method of Example 2.

The present application was further described in detail below in combination with FIGS. 1-2.

Examples of a Method for Separating Flavokawain and Kavalactone

Example 1 of the Separation Method

A method for separating flavokawain and kavalactone included the following specific steps:

S1. the root of *piper methysticum* was ground, 1 kg of powder of the *piper methysticum* root was weighed and added into a supercritical extraction kettle, then 50° C. of temperature and 8 MPa of pressure were set, supercritical $CO_2$ was added at a flow rate of 10 mL/min to perform extraction for 60 min. Then extracted oil and residue were collected. The yield of the extracted oil was 1.8% by weight, that is, the obtained extracted oil was 18 g. In the extracted oil, a total amount of flavokawain A and flavokawain B was 8.51 wt %, that is, 1.53 g. In the extracted oil, the content of kavalactone was 1.02 wt %, i.e. 0.18 g.

S2. the residue obtained in the step S1 was put into the supercritical extraction kettle again, then another extraction was performed at 60° C. of temperature, 20 MPa of pressure, and a supercritical $CO_2$ flow rate of 60 mL/min. The extraction was stopped after 180 min, then the residue was removed, and extracted oil was collected for later use. The yield of the extracted oil was 12.4 wt %, that is, the obtained extracted oil was 124 g. The content of kavalactone in the extracted oil was 75.43 wt %, i.e. 94 g. The content of flavokawain (flavokawain A and the flavokawain B) in the extracted oil was 2.02 wt %, i.e. 2.50 g.

S3. The extracted oil obtained in the step S2 was re-extracted and adsorbed. Specific steps were as follow: The extracted oil was dissolved in 80 Vol. % of methanol solution having a volume twice that of the extracted oil, and then n-hexane with equal volume of 80 Vol. % of methanol solution was added for re-extracting. The solution was sufficiently mixed under shaking, and left to stand, achieving a further separation of kavalactone and flavokawain (flavokawain A and the flavokawain B). The collected alcohol phase was used as an extraction mother solution, and the extraction mother solution was concentrated into an oil-like solution, which weighed 120 g, for later use. The concentrated extraction mother solution was dissolved in 80 Vol. % of methanol solution, heated up to 50° C., added with 1.2 g of adsorbent, left for absorption under stirring for 4 h, and then filtered to obtain a filtrate, and the obtained filtrate was concentrated into a paste, which weighed 90 g, for later use. The adsorbent was SephadexLH-20, that is, Sephadex LH.

S4. The paste obtained in the step S3 was dissolved in ethyl acetate having an addition amount of 0.5 times the weight of the paste, that is, 45 g. The solution was heated, added with petroleum ether slowly, and stirred at a rotary speed of 25 rpm, in which, volume ratio of ethyl acetate and petroleum ether was 8.5:1.8. When there was crystal appearing, the stirring was stopped, and the solution was left to stand for crystallization for 12 h, thereby obtaining kavalactone crystal.

Example 2 of the Separation Method

A method for separating flavokawain and kavalactone included the following specific steps:

S1. the root of *piper methysticum* was ground, 1 kg of powders of the *piper methysticum* root was weighed and added into a supercritical extraction kettle, and then 48° C. of temperature and 6 MPa of pressure were set, supercritical $CO_2$ was added at a flow rate of 30 mL/min to perform extraction for 120 min. Then extracted oil and residue were collected. The yield of the extracted oil was 2% by weight, that is, the obtained extracted oil was 20 g. In the extracted oil, the total amount of flavokawain A and flavokawain B was 10.04 wt %, that is, 2 g. In the extracted oil, the content of kavalactone was 1.5 wt %, i.e. 0.3 g. About 50% of flavokawain (flavokawain A and the flavokawain B) were removed by the step.

S2. the residue obtained in the step S1 was put into the supercritical extraction kettle again, then another extraction was performed at 70° C. of temperature and 35 MPa of pressure, and a supercritical $CO_2$ flow rate of 80 mL/min. The extraction was stopped after 150 min, then the residue was removed, and extracted oil was collected for later use. The yield of the extracted oil was 13 wt %, that is, the obtained extracted oil was 130 g. The content of kavalactone in the extracted oil was 85.62 wt %, i.e. 111.3 g. The content of flavokawain (flavokawain A and the flavokawain B) in the extracted oil was 2.53 wt %, i.e. 3.3 g.

S3. The extracted oil obtained in step S2 was re-extracted and adsorbed. Specific steps were as follow: the extracted oil was dissolved in a 90 Vol. % of ethanol having a volume 3.5 times that of the extracted oil, and then n-hexane with equal volume of 90 Vol. % of ethanol solution was added to for re-extracting. The solution was sufficiently mixed under shaking, and was left to stand, achieving a further separation of kavalactone and flavokawain (flavokawain A and the flavokawain B). The collected alcohol phase was used as an extraction mother solution, and the extraction mother solution was concentrated into oil-like solution, which weighed 125 g, for later use. The concentrated extraction mother solution was dissolved in 90 Vol. % of ethanol solution, heated up to 70° C., added with 4.6 g of adsorbent, left for adsorption under stirring for 5 h, and then filtered to obtain a filtrate, and the filtrate was concentrated into paste, which weighed 98 g, for later use. The adsorbent was a mixture of C18, silicone and activated carbon in a weight ratio of 1.2:5.3:3.5.

S4. The paste obtained by the step S3 was dissolved in methanol having an addition amount of 98 g. The solution was heated, added with dichloromethane slowly, and stirred at a rotary speed of 25 rpm, in which, volume ratio of methanol and dichloromethane was 9.2:1.8. When there was crystal appearing, stirring was stopped, and the solution was left to stand for crystallization for 20 h, thereby obtaining kavalactone crystal. Liquid chromatograms of flavokawain and kavalactone in the kavalactone crystal were shown in FIG. 1 and FIG. 2, respectively.

Example 3 of the Separation Method

A method for separating flavokawain and kavalactone included the following steps:

S1. the root of *piper methysticum* was ground, 1 kg of powder of the *piper methysticum* root were weighed and added into a supercritical extraction kettle, and then 45° C. of temperature and 4 MPa of pressure were set, supercritical $CO_2$ was added at a flow rate of 50 mL/min to perform extraction for 180 min. Then extracted oil and residue was collected. The yield of the extracted oil was 2.5% by weight, that is, the obtained extracted oil was 25 g. In the extracted oil, the total amount of flavokawain A and flavokawain B was 13.07 wt %, that is, 3.27 g. In the extracted oil, the content of kavalactone was 2.07 wt %, i.e. 0.5 g.

S2. the residue obtained in the step S1 was put into the supercritical extraction kettle again, another extraction was performed at 80° C. of temperature and 50 MPa of pressure, and a supercritical $CO_2$ flow rate of 100 mL/min. The extraction was stopped after 120 min, then the residue was removed, and extracted oil was collected for later use. The yield of the extracted oil was 11 wt %, that is, the obtained extracted oil was 110 g. The content of kavalactone in the extracted oil was 88.16 wt %, i.e. 97.0 g. The content of flavokawain (flavokawain A and the flavokawain B) in the extracted oil was 3.07 wt %, i.e. 3.4 g.

S3. The extracted oil obtained by the step S2 was re-extracted and adsorbed. Specific steps were as follow: the extracted oil was dissolved in a 95 Vol. % of ethanol having a volume 5 times the volume of the extracted oil, and then n-hexane with equal volume of 95 Vol. % of ethanol solution was added to for re-extracting. The solution was sufficiently mixed under shaking, and was left to stand, achieving a further separation of kavalactone and flavokawain (flavokawain A and the flavokawain B). The collected alcohol phase was used as an extraction mother solution, and the extraction mother solution was concentrated into oil-like solution, which weighed 122 g, for later use. The concentrated extraction mother solution was dissolved in 95 Vol. % of ethanol solution, heated up to 90° C., added with 6.7 g of adsorbent, left for adsorption under stirring for 8 h, and then filtered to obtain a filtrate, and the filtrate was concentrated into paste which weighed 103 g, for later use. The adsorbent was a mixture of silicone and activated carbon in a weight ratio of 5.3:3.5.

S4. The paste obtained by the step S3 was dissolved in acetone having an addition amount of acetone 2 times weight of the paste, that is, 206 g. The solution was heated, added with n-hexane slowly, and stirred at a rotary speed of 25 rpm, in which, volume ratio of acetone and n-hexane was 10:1.8. When there was crystal appearing, stirring was stopped, and the solution was left to stand for crystallization for 24 h, thereby obtaining kavalactone crystal.

Examples 4-11 of the Separation Method

The following examples differed from Example 2 in that process temperatures or process pressures were different in the supercritical extraction kettle of the steps S1 or S2, as shown in Table 1.

TABLE 1 process temperatures and pressures in the S1 and S2 of different examples

| Process parameter | step S1 | | step S2 | |
|---|---|---|---|---|
| | Process pressure/ MPa | Process temperature/ ° C. | Process pressure/ MPa | Process temperature/ ° C. |
| Example 2 | 6 | 48 | 35 | 70 |
| Example 4 | 4 | 48 | 35 | 70 |
| Example 5 | 8 | 48 | 35 | 70 |
| Example 6 | 6 | 45 | 35 | 70 |
| Example 7 | 6 | 50 | 35 | 70 |
| Example 8 | 6 | 48 | 20 | 70 |
| Example 9 | 6 | 48 | 50 | 70 |
| Example 10 | 6 | 48 | 35 | 60 |
| Example 11 | 6 | 48 | 35 | 80 |

Example 12 of the Separation Method

The present example differs from Example 2 in that the adsorbent used in the step S3 was different. Specifically, the adsorbent used in the present example was a mixture of C18, silicone and activated carbon in a weight ratio of 0.8:4.5:3. Other conditions were the same as those in Example 2.

Example 13 of the Separation Method

The present example differs from Example 2 in that the adsorbent used in the step S3 was different. Specifically, the adsorbent used in the present example was a mixture of C18, silicone and activated carbon in a weight ratio of 1.5:5.8:4. Other conditions were the same as those in Example 2.

Comparative Examples 1-8 of the Separation Method

The following comparative examples differed from Example 2 in that the process time or flow rate of supercritical $CO_2$ were different in the supercritical extraction kettle of the step S1 or S2 as shown in Table 2.

TABLE 2 process time and flow rate of supercritical $CO_2$ in the S1 and S2 of different examples

| Process parameter | step S1 | | step S2 | |
|---|---|---|---|---|
| | Process time/ min | Flow rate of supercritical $CO_2$/ (mL/min) | Process time/ min | Flow rate of supercritical $CO_2$/ (mL/min) |
| Example 2 | 120 | 30 | 150 | 80 |
| Comparative Example 1 | 40 | 30 | 150 | 80 |
| Comparative Example 2 | 200 | 30 | 150 | 80 |
| Comparative Example 3 | 120 | 5 | 150 | 80 |
| Comparative Example 4 | 120 | 55 | 150 | 80 |

TABLE 2-continued process time and flow rate of supercritical $CO_2$ in the S1 and S2 of different examples

| Process parameter | step S1 | | step S2 | |
|---|---|---|---|---|
| | Process time/ min | Flow rate of supercritical $CO_2$/ (mL/min) | Process time/ min | Flow rate of supercritical $CO_2$/ (mL/min) |
| Comparative Example 5 | 120 | 30 | 100 | 80 |
| Comparative Example 6 | 120 | 30 | 200 | 80 |
| Comparative Example 7 | 120 | 30 | 150 | 40 |
| Comparative Example 8 | 120 | 30 | 150 | 120 |

Comparative Examples 1-7 of the Separation Method

The following comparative examples differed Example 2 in that the process temperatures or pressures were different in the supercritical extraction kettle of the steps S1 or S2, as shown in Table 3.

TABLE 3 process temperatures and pressures in the S1 and S2 of different comparative examples

| Process parameters | step S1 | | step S2 | |
|---|---|---|---|---|
| | Process pressure/ MPa | Process temperature/ °C. | Process pressure/ MPa | Process temperature/ °C. |
| Example 2 | 6 | 48 | 35 | 70 |
| Comparative Example 1 | 2 | 48 | 35 | 70 |
| Comparative Example 2 | 12 | 48 | 35 | 70 |
| Comparative Example 3 | 6 | 40 | 35 | 70 |
| Comparative Example 4 | 6 | 55 | 35 | 70 |
| Comparative Example 5 | 6 | 48 | 15 | 70 |
| Comparative Example 6 | 6 | 48 | 35 | 55 |
| Comparative Example 7 | 6 | 48 | 35 | 85 |

Comparative Example 8 of the Separation Method

The present comparative example differed from Example 2 in that the step S1 was removed from the separation method, and the separation method was as follows:
S1. the root of *piper methysticum* was ground, 1 kg of powders of the *piper methysticum* root were weighed and added into a supercritical extraction kettle, and then 70° C. of temperature and 35 MPa of pressure were set, supercritical $CO_2$ was added at a flow rate of 80 mL/min and extracted for 150 min. Then residue was removed, and extracted oil was collected for later use.
S2. Specific steps were same as those in step S3 of Example 2.
S3. Specific steps were same as those in step S4 of Example 2, by which kavalactone crystal was obtained. The content of kavalactone in the kavalactone crystal was 93.64 wt %, and total amount of flavokawain A and the flavokawain B was 1.21 wt %.

Comparative Example 9 of the Separation Method

The present comparative example differed from Example 2 in that, merely a re-extraction process was included in the step S3 of the separation method, and the separation method were as follow:
S1 and S2 were same as the S1 and the S2 of Example 2, and 130 g of extracted oil was obtained.
S3. extracted oil obtained in the step S2 was re-extracted. Specific steps were as follow: the extracted oil was dissolved in a 90 Vol. % of ethanol having a volume 3.5 times the volume of the extracted oil, and then petroleum ether with equal volume of 90 Vol. % of ethanol solution was added for re-extracting. The solution was sufficiently mixed under shaking, and was left to stand, achieving a further separation of kavalactone and flavokawain (flavokawain A and the flavokawain B). The collected alcohol phase was extraction mother solution, the extraction mother solution was concentrated into oil-like solution, which weighed 125 g, for later use.
S4. The extraction mother solution concentrated into oil-like solution obtained in the step S3 was dissolved in 125 g of methanol, and treated by the same subsequent steps as those in Example 2, thereby obtaining the kavalactone crystal.

Comparative Example 10 of the Separation Method

The comparative example differed from Example 2 in that, merely an adsorption process was performed in the step S3 of the separation method, and the separation method was as follows:
S1 and S2 were same as the S1 and the S2 of Example 2, and 130 g of extracted oil was obtained.
S3. The extracted oil obtained in the step S2 was adsorbed. Specific steps were as follow: the extracted oil was dissolved in 90 Vol. % of ethanol solution; and the dissolved solution was heated up to 70° C., added with 4.6 g of adsorbent, and left for adsorption under stirring for 5 h, and then filtered to obtain a filtrate, and the filtrate was concentrated into paste for later use. The adsorbent was a mixture of C18, silicone and activated carbon in a weight ratio of 1.2:5.3:3.5.
S4 was same as the S4 of Example 2.

Comparative Example 11 of the Separation Method

The present comparative example differed from Example 2 in that adsorption process was firstly performed and re-extraction process was secondly performed. The separation method was as follows:
S1 and S2 were same as the S1 and the S2 of Example 2, and 130 g of extracted oil was obtained.
S3. The extracted oil obtained by the step S2 was adsorbed. Specific steps were as follow: The extracted oil was dissolved in a 90 Vol. % of ethanol having a volume 3.5 times the volume of the extracted oil, and the dissolved solution was heated up to 70° C., added with 4.6 g of adsorbent, left for adsorption under stirring for 5 h, and then filtered to obtain a filtrate, and the filtrate was concentrated into paste for later use. The adsorbent was a mixture of C18, silicone and activated carbon in a weight ratio of 1.2:5.3:3.5.
The concentrated into paste-like filtrate was dissolved in 90 Vol. % of ethanol having a volume 3.5 times the volume of the paste-like filtrate; and then petroleum ether with equal volume of 90 Vol. % ethanol solution was added for re-extracting. The solution was sufficiently mixed under shaking, and was left to stand, achieving a further separation of kavalactone and flavokawin (flavokawain A and the flavokawain B). The collected alcohol phase was used as extraction mother solution, and the extraction mother solution was concentrated into oil-like solution for later use.

S4. The oil-like concentrated extraction mother solution was dissolved in methanol, and then treated by the same subsequent steps as those in Example 2, thereby obtaining kavalactone crystal.

Performance Tests Experiments

The detection of contents of kavalactone and flavokawin A and the flavokawin B were public in the literature of *Piper methysticum Rootstock Dry Extract on the Herbal Medicines Compendium*; and the contents were tested by using a high-performance Liquid Chromatographic. Results were shown in Table 4.

TABLE 4 the content of kavalactone and flavokawin in the products obtained from each stage in different examples

| Embodiment | | Example 1 | Example 2 | Example 3 | Example 4 | Example 5 | Example 6 | Example 7 |
|---|---|---|---|---|---|---|---|---|
| After being treated by step S1 | Yield of extracted oil % | 1.8 | 2.0 | 2.5 | 1.8 | 2.5 | 1.8 | 2.1 |
| | Content of kavalactone in the extracted oil % | 8.51 | 10.04 | 13.07 | 8.92 | 12.63 | 8.97 | 12.53 |
| | Contents of A and B in the extracted oil % | 1.02 | 1.54 | 2.07 | 1.36 | 1.92 | 1.31 | 2.06 |
| After being treated by step S2 | Yield of extracted oil %% | 12.4 | 13.0 | 11.0 | 12.9 | 13.0 | 13.1 | 12.9 |
| | Content of kavalactone in the extracted oil % | 75.43 | 85.62 | 88.16 | 85.33 | 85.21 | 85.29 | 85.47 |
| | Contents of A and B in the extracted oil % | 2.02 | 2.53 | 3.07 | 3.04 | 2.35 | 3.17 | 2.51 |
| Kavalactone crystal | Content of kavalactone/% | 98.12 | 99.02 | 98.51 | 98.68 | 99.22 | 98.56 | 99.12 |
| | Contents of A and B % | 0.05 | 0.05 | 0.07 | 0.07 | 0.05 | 0.08 | 0.04 | the content of kavalactone and flavokawin in the products obtained from each stage in different examples

| Embodiment | | Example 8 | Example 9 | Example 10 | Example 11 | Example 12 | Example 13 | Comparative Example 1 |
|---|---|---|---|---|---|---|---|---|
| After being treated by step S1 | Yield of extracted oil % | 2.0 | 2.1 | 2.0 | 1.9 | 2.0 | 2.1 | 1.4 |
| | Content of kavalactone in the extracted oil % | 10.05 | 10.03 | 10.05 | 10.02 | 10.01 | 10.04 | 8.63 |
| | Contents of A and B in the extracted oil % | 1.51 | 1.54 | 1.52 | 1.54 | 1.53 | 1.51 | 1.31 |
| After being treated by step S2 | Yield of extracted oil % | 11.5 | 13.3 | 11.2 | 13.7 | 13.0 | 13.0 | 12.8 |
| | Content of kavalactone in the extracted oil % | 85.03 | 86.21 | 84.82 | 87.12 | 85.67 | 85.21 | 85.56 |
| | Contents of A and B in the extracted oil % | 2.42 | 2.69 | 2.54 | 2.93 | 2.49 | 2.52 | 3.32 |
| Kavalactone crysta | Content of kavalactone/% | 99.39 | 99.11 | 99.54 | 99.06 | 99.23 | 99.41 | 98.31 |
| | Contents of A and B % | 0.05 | 0.08 | 0.05 | 0.06 | 0.06 | 0.03 | 0.15 | the content of kavalactone and flavokawin in the products obtained

TABLE 4-continued from each stage in different examples

| Embodiment | | Comparative Example 2 | Comparative Example 3 | Comparative Example 4 | Comparative Example 5 | Comparative Example 6 | Comparative Example 7 | Comparative Example 8 |
|---|---|---|---|---|---|---|---|---|
| After being treated by step S1 | Yield of extracted oil % | 2.8 | 1.2 | 2.7 | 2.0 | 2.1 | 1.9 | 2.0 |
| | Content of kavalactone in the extracted oil % | 14.92 | 8.54 | 14.53 | 10.02 | 10.06 | 10.01 | 10.05 |
| | Contents of A and B in the extracted oil % | 1.97 | 1.16 | 1.92 | 1.52 | 1.54 | 1.50 | 1.53 |
| After being treated by step S2 | Yield of extracted oil % | 13.0 | 12.9 | 13.1 | 10.5 | 13.7 | 10.2 | 13.8 |
| | Content of kavalactone in the extracted oil % | 85.43 | 85.52 | 85.56 | 84.01 | 82.25 | 83.24 | 86.94 |
| | Contents of A and B in the extracted oil % | 2.73 | 3.36 | 2.81 | 2.48 | 2.42 | 3.12 | 2.81 |
| Kavalactone crysta | Content of kavalactone/% | 98.63 | 98.42 | 98.02 | 98.02 | 98.82 | 98.21 | 99.01 |
| | Contents of A and B % | 0.12 | 0.16 | 0.14 | 0.09 | 0.15 | 0.18 | 0.15 | the content of kavalactone and flavokawain in the products obtained from each stage in different examples

| Embodiment | | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|
| After being treated by step S1 | Yield of extracted oil % | 0.8 | 3.2 | 1.2 | 3.0 | 2.1 | 2.0 | 1.9 |
| | Content of kavalactone in the extracted oil % | 5.21 | 20.32 | 7.55 | 18.01 | 10.06 | 10.02 | 10.01 |
| | Contents of A and B in the extracted oil % | 0.52 | 2.51 | 1.04 | 2.64 | 1.52 | 1.51 | 1.49 |
| After being treated by step S2 | Yield of extracted oil % | 13.1 | 13.2 | 13.0 | 12.9 | 8.6 | 9.3 | 13.8 |
| | Content of kavalactone in the extracted oil % | 86.33 | 88.26 | 87.63 | 88.03 | 80.13 | 81.42 | 88.06 |
| | Contents of A and B in the extracted oil % | 7.13 | 4.01 | 6.84 | 4.06 | 5.04 | 4.51 | 3.82 |
| Kavalactone crysta | Content of kavalactone/% | 95.82 | 97.13 | 97.16 | 97.89 | 96.28 | 97.32 | 93.26 |
| | Contents of A and B % | 1.22 | 0.48 | 1.06 | 0.50 | 1.03 | 0.84 | 0.36 |

TABLE 4-continued the content of kavalactone and flavokawain in the products obtained from each stage in different examples

| Embodiment | | Comparative ple 8 | Comparative ple 9 | Comparative Example 10 | Comparative Example 11 |
|---|---|---|---|---|---|
| After being treated by step S1 | Yield of extracted oil % | / | 2.1 | 2.1 | 2.0 |
| | Content of kavalactone in the extracted oil % | / | 10.04 | 10.04 | 10.03 |
| | Contents of A and B in the extracted oil % | / | 1.52 | 1.51 | 1.53 |
| After being treated by step S2 | Yield of extracted oil % | / | 13.1 | 13.0 | 13.2 |
| | Content of kavalactone in the extracted oil % | / | 85.57 | 85.61 | 85.7 |
| | Contents of A and B in the extracted oil % | / | 2.56 | 2.53 | 2.56 |
| Kavalactone crysta | Content of kavalactone % | 93.64 | 98.63 | 98.82 | 98.84 |
| | Contents of A and B % | 1.21 | 0.51 | 0.92 | 0.74 |

Comparing the results of Example 2, Examples 4-5 and Comparative Examples 1-2, it can be seen that, in step S1, it is suggested that the extraction pressure should be set as 4-8 MPa in the step S1: when the extraction pressure is lower than 4 MPa (Comparative Example 1), it resulted in a poor separation efficiency of flavokawain (flavokawain A and the flavokawain B), and a large amount of flavokawain (flavokawain A and the flavokawain B) was remained in the residue, such that a large amount of flavokawain (flavokawain A and the flavokawain B) were extracted together with kavalactone in the step S2; however, flavokawain (flavokawain A and the flavokawain B) and kavalactone were not sufficiently separated by re-extraction and adsorption, therefore the content of flavokawain (flavokawain A and the flavokawain B) in the obtained kavalactone crystal was relatively high. When the pressure was higher than 8 MPa (comparative Example 2), a large amount of kavalactone and flavokawain (flavokawain A and the flavokawain B) was extracted together and discarded as waste liquid, which directly resulted in excessive loss of kavalactone; meanwhile, cells of raw materials were damaged by excessive extraction pressure in the extraction process of S1, such that containing inside the cells were more easily extracted, therefore, after re-extraction of S2 was finished, the content of flavokawain (flavokawain A and the flavokawain B) were higher in the extracted oil, and the content of other impurities were also higher. Therefore, considering from two aspects, that is, the utilization rate of kavalactone and the content of flavokawain in kavalactone crystal, extraction pressure of more than 8 MPa in the step S1 was not suggested.

Comparing the results of Example 2, Examples 6-7 and Comparative Examples 3-4, it can be seen that, it is suggested that extraction temperature in the step S1 should be set as 45-50° C.: when the extraction temperature was lower than 45° C. (Comparative Example 3), it also resulted in that a large amount of flavokawain (flavokawain A and the flavokawain B) was remained in the residue, thereby a large amount of flavokawain (flavokawain A and the flavokawain B) was extracted together with kavalactone in the step S2, finally the content of flavokawain (flavokawain A and the flavokawain B) in the obtained kavalactone crystal was relatively higher; and when the temperature was higher than 50° C. (Comparative Example 4) in the step S1, it also resulted in problems such as excessive loss of kavalactone, high content of flavokawain (flavokawain A and the flavokawain B). Therefore extraction temperature of more than 50° C. in the step S1 was not suggested.

Comparing the test results of Example 2, Examples 8-9 and Comparative Examples 5, it can be seen that, it is suggested that extraction pressure in the step S2 should be set as 20-50 MPa: when the extraction pressure was lower than 20 MPa (Comparative Example 5), it resulted in that a large amount of kavalactone were remained in the residue and discarded as waste material, therefore, considering from the utilization rate of kavalactone, extraction pressure of lower than 20 MPa in the step S2 was not suggested; and, under an extraction pressure of lower than 20 MPa, flavokawain (flavokawain A and the flavokawain B) was more easily extracted, which resulted in a problem of high content on flavokawain (flavokawain A and the flavokawain B) in the kavalactone crystal. In addition, considering an affordable pressure for the equipment, an extraction pressure of more than 8 MPa was not suggested.

Comparing the results of Example 2, Examples 10-11 and comparative Examples 6-7, it can be seen that, it is suggested that extraction temperature should be set as 60-80°° C. in the step S2: when the extraction temperature was lower than 60° C. (Comparative Example 6), it also resulted in that a large amount of kavalactone were remained in the residue and discarded as waste materials; in addition, the lower temperature was more suitable for extraction of flavokawain (flavokawain A and the flavokawain B), so that there was a poor separation efficiency of kavalactone and flavokawain (flavokawain A and the flavokawain B). Therefore, considering from two aspects, that is, the utilization rate of kavalactone and separation efficiency of kavalactone and flavokawain (flavokawain A and the flavokawain B), the temperature of lower than 60° C. is not suggested. When temperature was higher than 80° C. (comparative Example 7), other impurities except for kavalactone and flavokawain (flavokawain A and the flavokawain B) were extracted, which directly resulted in more and more impurities in the kavalactone crystal and low content of kavalactone.

In the process, the influence of extraction pressure and temperature on separation efficiency is significant, meanwhile, extraction time and flow rate of supercritical $CO_2$ are also one of parameters promising technical effects.

Comparing the results of Example 2 and Comparative Examples 1-2, it can be seen that, it is suggested that, extraction time should be set in a range of 60-80 min. When the extraction time was higher than 180 min (Comparative Example 2), separation efficiency of kavalactone and flavokawain will be reduced, and the content of flavokawain (flavokawain A and the flavokawain B) in the kavalactone crystal will be increased. That's because a sufficient separation can be achieved between flavokawain (flavokawain A and the flavokawain B) and kavalactone of the residue in the step S1, however, a greater degree of damage to cells of *piper methysticum* in the step S1 can be caused by excessive extraction time, so the containing inside the cells were more easily extracted. After the residue was processed by the step S2, kavalactone was extracted with more flavokawain (flavokawain A and the flavokawain B) and other impurities, resulting in a relatively high content of flavokawain (flavokawain A and the flavokawain B) in the obtained kavalactone crystal.

Comparing the test results of Example 2, Comparative Examples 3-4, it can be seen that flow rate of supercritical $CO_2$ for extracting in the step S2 was recommended in the range of 10-50 mL/min. Exceeding the range will also had an impact on the separation efficiency of kavalactone and flavokawain.

In addition, Comparative Examples 5-8 can be seen that separation efficiency was affected by extraction time and flow rate of supercritical $CO_2$ in the step S2. The yield of extracted oil was affected by a short extraction time of Comparative Example 5, and the extraction of kavalactone was not sufficient, resulting in a relatively high proportion of flavokawain (flavokawain A and the flavokawain B) in the extracted oil, and a relatively high content (0.09 wt %) of flavokawain (flavokawain A and the flavokawain B) in the obtained kavalactone crystal. The extraction time was excessively long in the Comparative Example 6, other impurities were extracted with kavalactone and flavokawain (flavokawain A and the flavokawain B), therefore, the relative content of kavalactone was reduced, however, the content (0.09 wt %) of flavokawain (flavokawain A and the flavokawain B) in the obtained kavalactone crystal was higher. Likewise, flow rate of supercritical $CO_2$ had a similar impact on separation efficiency. High content of flavokawain (flavokawain A and the flavokawain B) in the kavalactone crystal was caused by the flow rate of supercritical $CO_2$ was lower than 60 mL/min or higher than 100 mL/min in the Comparative Example 7.

However, among the four extraction parameters (temperature, pressure, time and flow rate of supercritical $CO_2$) of S1 and S2, temperature and pressure had a relatively greater impact on separation efficiency, and time and flow rate of supercritical $CO_2$ had a less impact on separation efficiency.

However, comparing the test results of Example 2 and comparative Example 8, it can be seen that kavalactone and flavokawain (flavokawain A and the flavokawain B) were separated by using extraction method of high temperature and pressure, which is difficult to achieve the purpose of effective separation, such as there was still 1.21 wt % of flavokawain in the obtained kavalactone crystal.

Further combining comparative Examples 9-11, it can be seen that re-extraction and adsorption were also important to the separation of kavalactone and flavokawain. Firstly, the separation of kavalactone and flavokawain can be achieved by using re-extraction method, secondly, the separation of kavalactone and flavokawain can be achieved by using adsorption. It was not recommended that the separation of kavalactone and flavokawain can be achieved by using first re-extraction and second adsorption in the technical solution, otherwise it is difficult to achieve separation efficiency, and the content of flavokawain in the obtained kavalactone crystal was still higher than 0.1 wt %.

Examples of the Microencapsulated Kavalactone

Example 1 of the Microencapsulated Kavalactone

The microencapsulated kavalactone includes an inner core and an outer cladding layer, raw materials of the inner core were as follow: kavalactone crystal and 85 Vol. % of ethanol solution, raw materials of the outer cladding layer were as follow: excipient, film former and water. The weight ratio of excipient and kavalactone was 1:1; the excipient was a combination of emulsified starch and dextrine in a weight ratio of 1:1. Film former was xanthan gum, and the weight ratio of the film former and the excipient was 1:100. Kavalactone crystal was obtained by using the separation method of Example 1.

A method for preparing the microencapsulated kavalactone was as follows:

I. Preparation of oil phase: dissolving 200 g of kavalactone crystal in 85-95 Vol. % of ethanol solution, then concentrating into a grease, and storing at 75° C. for later use;

preparation of water phase: dissolving 200 g of excipient into 1600 g of hot water with 80° C. for later use;

II. Adding the oil phase into the water phase in the high-speed shearing with 8000 rpm of rotation rate, then adding xanthan gum, and shearing for 30 min at the high-speed, and then spray-drying at 80° C. to obtain the microencapsulated kavalactone. The microencapsulated kavalactone can be stored for 24 months at the room temperature.

Example 2 of the Microencapsulated Kavalactone

The microencapsulated kavalactone includes an inner core and an outer cladding layer, raw materials of the inner core were as follow: kavalactone crystal and 90 Vol. % of ethanol solution, raw materials of the outer cladding layer were as follow: excipient, film former and water. The weight ratio of excipient and kavalactone was 22:10; the excipient was a combination of emulsified starch and dextrine in a weight ratio of 4:1. Film former was arabic gum, and the weight ratio of the film former and the excipient was 2:100. Kavalactone crystal was obtained by using the separation method of Example 2.

A method for preparing the microencapsulated kavalactone was as follows:

I. Preparation of oil phase: dissolving 200 g of kavalactone crystal in 90 Vol. % of ethanol solution, then concentrating into a grease, and storing at 80° C. for later use;

preparation of water phase: dissolving 440 g of excipient into 3960 g of hot water with 90° C. for later use;

II. Adding the oil phase into the water phase in the high-speed shearing with 10000 rpm of rotation rate, then adding 0.88 g of arabic gum, and shearing for 45 min at the high-speed, and then spray-drying at 85° C. to obtain the microencapsulated kavalactone. The microencapsulated kavalactone can be stored for 26 months at the room temperature. The content of kavalactone was 30.52 wt % in the microencapsulated kavalactone.

Example 3 of the Microencapsulated Kavalactone

The microencapsulated kavalactone includes an inner core and an outer cladding layer, raw materials of the inner core were as follow: kavalactone crystal and 95 Vol. % of ethanol solution, raw materials of the outer cladding layer were as follow: excipient, film former and water. The weight ratio of excipient and kavalactone was 20:1; the excipient was a combination of emulsified starch and dextrine in a weight ratio of 10:1. Film former was carrageenan, and the weight ratio of the film former and the excipient was 3:100. Kavalactone crystal was obtained by using the separation method of Example 3.

A method for preparing the microencapsulated kavalactone was as follows:

I. Preparation of oil phase: dissolving 200 g of kavalactone crystal in 95 Vol. % of ethanol solution, then concentrating into a grease, and storing at 82° C. for later use;

preparation of water phase: dissolving 4 kg of excipient into 40 kg of hot water with 100° C. for later use;

II. Adding the oil phase into the water phase in the high-speed shearing with 12000 rpm of rotation rate, then adding 0.88 g of carrageenan, and shearing for 60 min at the high-speed, and then spray-drying at 90° C. to obtain the microencapsulated kavalactone. The microencapsulated kavalactone can be stored for 25 months at the room temperature.

Example 4 of the Microencapsulated Kavalactone

Comparing the microencapsulated kavalactone of Example 2, the difference was that there was no film former in the raw material of the packing layer, other components were same as the microencapsulated kavalactone of Example 2.

While preparing the microencapsulated kavalactone, the step of I was same as the microencapsulated kavalactone of Example 2, the step of II was as follows:

II. Adding the oil phase into the water phase in the high-speed shearing with 10000 rpm of rotation rate, shearing for 45 min at the high-speed, and then spray-drying at 85° C. to obtain the microencapsulated kavalactone. The microencapsulated kavalactone can be stored for 26 months at the room temperature.

If kavalactone crystal was not microencapsulated, shelf life of kavalactone crystal will be cut to 5-7 months. That was because part grease was contained in the obtained kavalactone crystal, the untreated grease was prone to going bad, such that the shelf life of kavalactone crystal was shorter. After microencapsulated treatment, the grease contained in the kavalactone crystal was adsorbed in the excipient, which was not prone to contact with air, thereby achieving the purpose of improving shelf time.

The above are the preferred embodiments of the present application, which are not intended to limit the protection scope of the present application. Therefore, all equivalent changes made according to the structure, shape and principle of the present application should be covered within the protection scope of the present application.

What is claimed is:

1. A method for separating flavokawain and kavalactone, comprising the steps of:

step S1: grinding root of *piper methysticum*, extracting by supercritical carbon dioxide and collecting a residue, wherein an extraction temperature during the step S1 is 45-50° C. and an extraction pressure during the step S1 is 4-8 MPa;

step S2: extracting the residue by the supercritical carbon dioxide, and collecting extracted oil, wherein an extraction temperature during the step S2 is 60-80° C. and an extraction pressure during the step S2 is 20-50 MPa;

step S3: performing re-extraction and an adsorption treatment on the extracted oil to obtain a primary product of the kavalactone; and step S4: crystallizing the primary product of the kavalactone to obtain the kavalactone;

wherein the kavalactone is a mixture of six compounds, comprising: Methysticin, Dihydromethystcin, Kavain, Dihydrokavain, Yangonin and Desmethoxyangonin;

wherein the re-extraction in the step S3 comprises the steps of:

dissolving the extracted oil in a first solvent; and performing the re-extraction by using a re-extraction solvent to obtain an extraction mother solution, wherein the first solvent is 80-95 vol. % of an ethanol solution or 80-95 vol. % of a methanol solution, and the re-extraction solvent is one or more of N-hexane, petroleum ether, or ether;

wherein the adsorption treatment in the step S3 uses an adsorbent, and the adsorbent is one or more selected from a group consisting of silicone, alumina, activated carbon, C18, polyamide, and Sephadex LH-20.

2. The method according to claim 1, wherein, in the step S1, an extraction time is 60-180 min, and a flow rate of the supercritical carbon dioxide is 10-50 mL/min; and, in step S2, an extraction time is 120-180 min, and a flow rate of the supercritical carbon dioxide is 60-100 mL/min.

3. The method according to claim 1, wherein an adsorption temperature in the step S3 is 50-90° C.

4. The method according to claim 1, wherein the adsorbent is a mixture of the C18, the silicone and the activated carbon in a weight ratio of (0.8-1.5):(4.5-5.8):(3-4).

5. The method according to claim 1, wherein the crystallizing in the step S4 comprises the following steps: dissolving the primary product of the kavalactone in a second solvent, heating, then adding a third solvent, stirring until a crystal appears, and standing for solid-fluid separation to obtain a kavalactone crystal.

6. The method according to claim 5, wherein a heating temperature in the step S4 is 40-80° C., the second solvent is one or more selected from a group consisting of methyl acetate, methyl butanone, methanol, ethanol, acetone, and ethyl acetate, and the third solvent is one or more selected from a group consisting of the petroleum ether, the N-hexane, and dichloromethane.

* * * * *